United States Patent [19]
Kubota et al.

[11] Patent Number: 5,697,939
[45] Date of Patent: Dec. 16, 1997

[54] APPARATUS FOR HOLDING A MEDICAL INSTRUMENT IN PLACE

[75] Inventors: Tatsuya Kubota, Sagamihara; Takashi Fukaya, Tokyo; Koji Yasunaga, Tokyo; Masanori Kaneda, Tokyo; Hitoshi Karasawa, Tokyo; Kyo Imagawa, Tokyo; Tetsumaru Kubota, Tokyo; Hideyuki Adachi, Tokyo; Yoshinao Oaki, Tokyo; Kenji Yoshino, Tokyo; Masaya Yoshihara, Tokyo; Hitoshi Mizuno, Tokyo; Akihiro Taguchi, Tokyo; Yoshihiro Kosaka, Shirakawa; Masaaki Hayashi, Tokyo, all of Japan

[73] Assignee: Olympus Optical Co., Ltd., Tokyo, Japan

[21] Appl. No.: 423,301

[22] Filed: Apr. 18, 1995

Related U.S. Application Data

[63] Continuation of Ser. No. 106,819, Aug. 16, 1993, abandoned.

[30] Foreign Application Priority Data

Aug. 20, 1992 [JP] Japan .................. 4-221571
Jul. 21, 1993 [JP] Japan .................. 5-180116

[51] Int. Cl.⁶ .................................. A61B 19/00
[52] U.S. Cl. .................................. 606/130
[58] Field of Search ............... 606/130, 1; 128/70; 600/200, 201, 204, 207

[56] References Cited

U.S. PATENT DOCUMENTS

| | | | |
|---|---|---|---|
| 3,115,140 | 12/1963 | Volkman | 606/130 |
| 4,573,452 | 3/1986 | Greenberg . | |
| 4,608,977 | 9/1986 | Brown | 606/130 |
| 4,617,916 | 10/1986 | Le Vahn et al. . | |
| 4,706,665 | 11/1987 | Gouda | 606/130 |
| 5,030,223 | 7/1991 | Anderson et al. | 606/130 |
| 5,047,036 | 9/1991 | Koutrouvelis | 606/130 |
| 5,221,283 | 6/1993 | Chang | 606/1 |
| 5,246,448 | 9/1993 | Chang | 606/1 |
| 5,273,039 | 12/1993 | Fujiwara et al. | 606/130 |
| 5,305,203 | 4/1994 | Raab | 606/130 |
| 5,308,352 | 5/1994 | Koutrouvelis | 606/130 |
| 5,320,628 | 6/1994 | Ufkin | 606/130 |

FOREIGN PATENT DOCUMENTS 1-130304 9/1989 Japan .

*Primary Examiner*—Glenn Dawson
*Attorney, Agent, or Firm*—Frishauf, Holtz, Goodman, Langer & Chick

[57] ABSTRACT

An apparatus for holding a medical instrument, such as an endoscope, in place without exerting an undue force on an insertion hole in an abdominal cavity of a subject even when the arm of a scope-holding section is unlocked, includes a four-link parallelogram mechanism. The four-link parallelogram mechanism includes a support arm for supporting a treating tool, an arm section parallel to the support arm and upper and lower arm sections connected to the upper and lower end sides of the support arm and arm section in a parallel relation. A support mechanism supports the arm sections of the four-link parallelogram mechanism to allow the arm sections to be moved in left/right and up/down directions, while being rotated, so that a straight line connecting an intersecting point P of a center line of the treating instrument inserted into an insertion hole in an abdominal wall of a subject and the center of the insertion hole to spherical bearings of the arm is set parallel to the upper and lower arm sections.

18 Claims, 8 Drawing Sheets

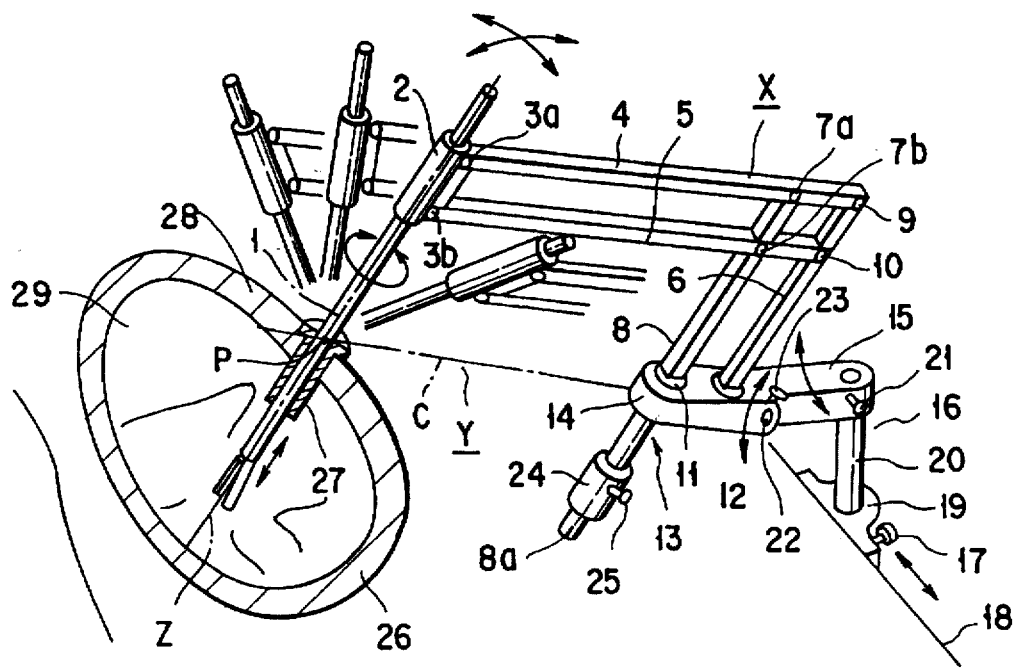
F I G. 1
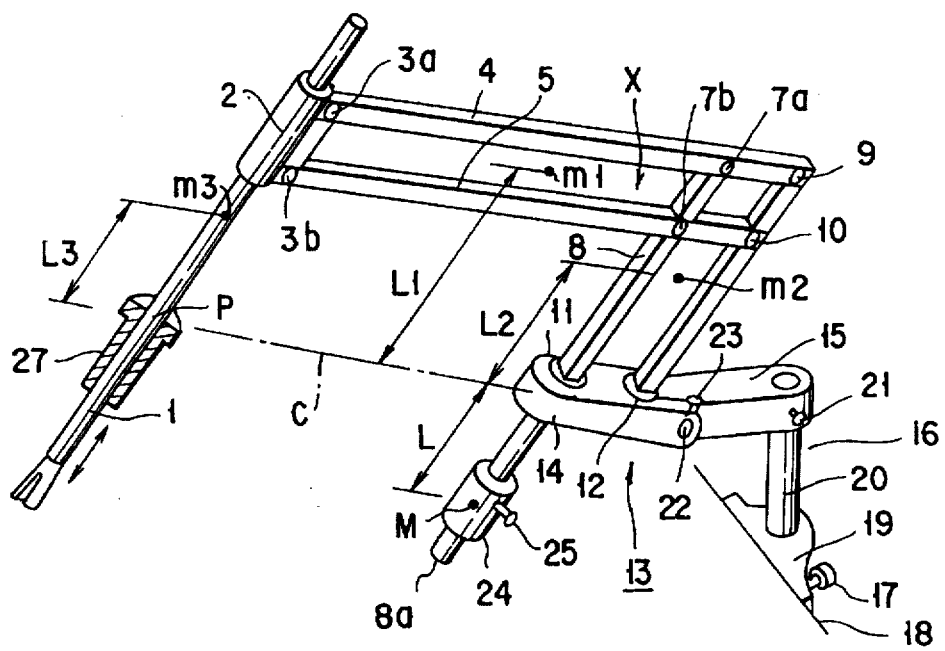
F I G. 2

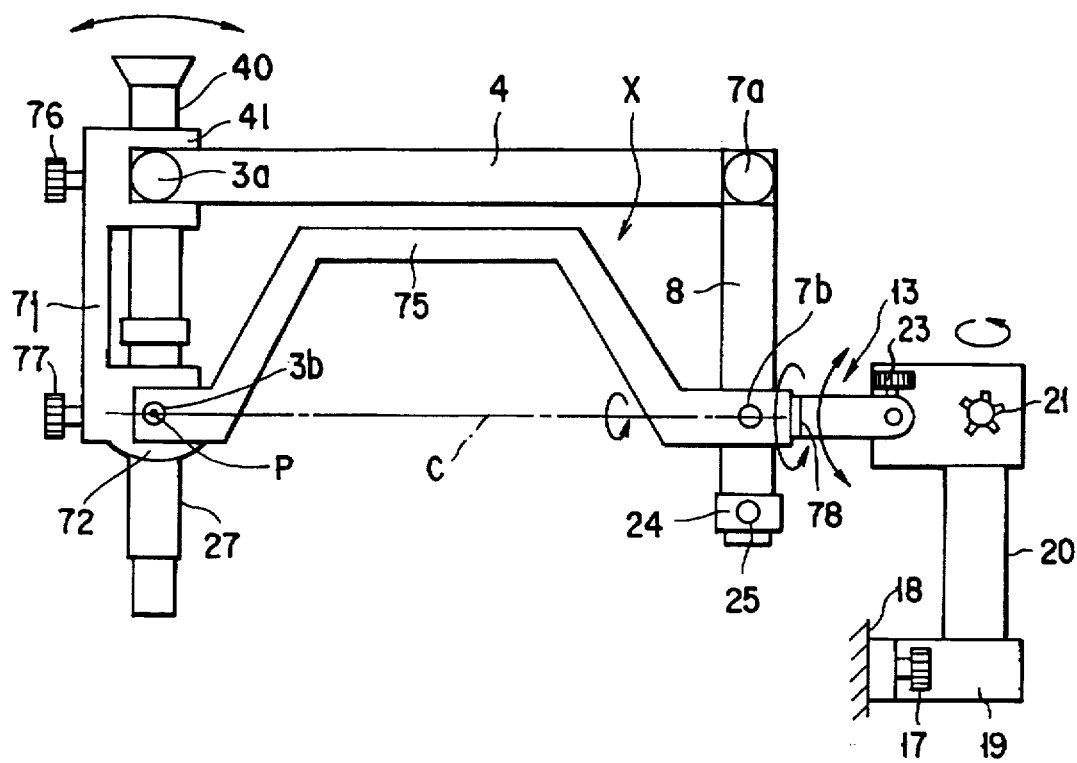
F I G. 14
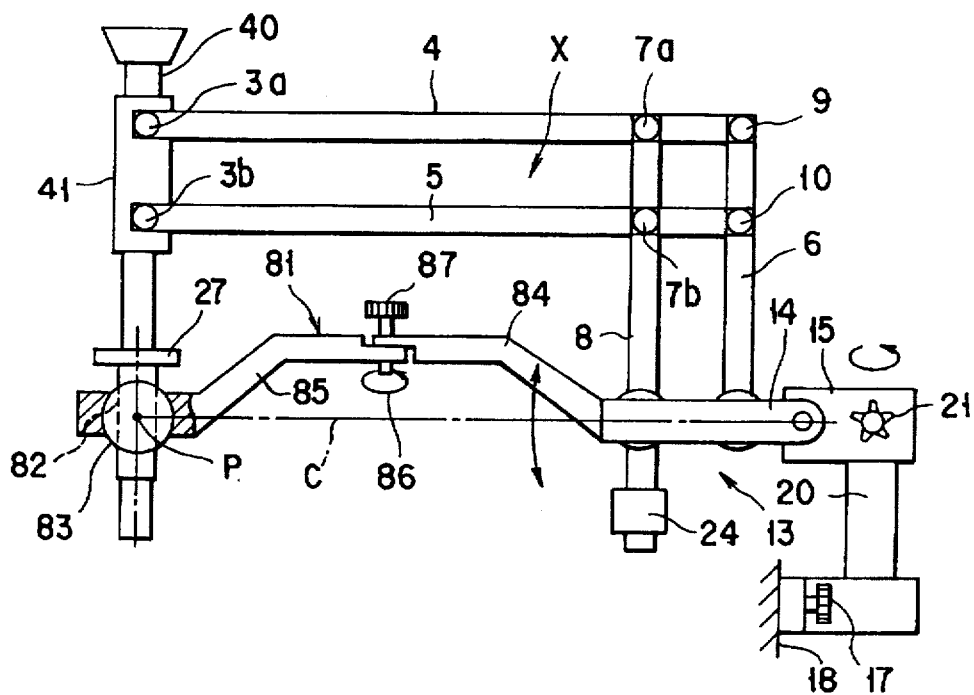
F I G. 15

5,697,939

APPARATUS FOR HOLDING A MEDICAL INSTRUMENT IN PLACE

This application is a Continuation of application Ser. No. 08/106,819, filed Aug. 16, 1993, now abandoned.

BACKGROUND OF THE INVENTION

1. Field of the Invention

The present invention relates to an apparatus and method for holding in place, instead of an operator's hand, a medical instrument, such as a treating instrument inserted into, for example, an abdominal cavity of a patient as well as an endoscope.

2. Description of the Related Art

A plurality of treating instruments, such as a laparoscope, are often used at the same time in an operation on a patient. In the operation involved, these treating instruments are used in a complicated situation while holding the laparoscope, etc., directly by hand. It is, therefore, difficult to perform such an operation under a situation in which these instruments are used at the same time.

During the time in which a ROI (region of interest) in the abdominal cavity of a patient is observed under the laparoscope, for example, if the operator has to change the direction in which observation is made, it needs to be so done by hand with the laparoscope held gripped by the same hand.

Further, upon surgery, the operating staff is at a patient's bedside in a narrow operation room at all times, while another staff member holding the laparoscope, etc., is also standing near the patient at the same time. No better operability is, therefore, secured under this situation.

Jpn.UM.Appln. KOKAI Publication No. 1-130304 discloses a scope-holder which is used to hold in place, instead of the operation hand, a treating instrument inserted into the abdominal cavity of a patient as well as a laparoscope, etc. The scope-holder has a plurality of arms, on one of which a holder section is provided with an engaging section formed thereon. An associated engaging member mounted on the endoscope is moved in a plane substantially perpendicular to a direction in which the endoscope is inserted, and engages with the first mentioned engaging member and is fixedly held there.

The conventional scope-holder as set out above fixedly holds the endoscope in place with the arm locked, but, when the arm is unlocked so as to move the endoscope, the arm becomes unsteady in its position. This imparts an undue force to an insertion hole, through which a trocar is thrust into the abdominal cavity of the patient, and involves a risk that the endoscope due to start falling down with its own weight. Further, once the arm is unlocked, a complex operation has to be restarred so as to adjust the endoscope to be at the proper place.

SUMMARY OF THE INVENTION

It is accordingly the object of the present invention to provide an apparatus and method for holding a medical instrument in proper place, without imparting any undue force to the abdominal wall, etc., even when the medical instrument is displaced.

According to one aspect of the present invention there is provided a holding apparatus for holding in place a medical instrument inserted into an insertion hole in a body wall of a human subject, comprising:

holding means for holding the medical instrument in place; and a parallel link mechanism for imparting to the medical instrument a motion about a substantial center corresponding to an intersecting point of a center line of the medical instrument held by the holding means and center of the insertion hole.

According to another aspect of the present invention, a holding apparatus a first mechanism for imparting to the medical instrument a tilt motion about a substantial center corresponding to an intersecting point of a center line of a medical instrument held by a holding means and center of the insertion hole; and a second mechanism supporting the first mechanism and imparting to the medical instrument a rotational motion about a straight line substantially passing through the intersecting point and intersecting the center line of the medical instrument.

According to another aspect of the present invention, a method is provided for holding a medical instrument in place when a medical operation is to be performed on a subject with the medical instrument thrust into an insertion hole of the body wall of the human subject, the method comprising the steps of:

setting the medical instrument relative to a position near the insertion hole; and simultaneously rotating the medical instrument and a trocar about a non-movable point, the trocar receiving the medical instrument.

According to the present apparatus and method, the treating instrument and medical instrument such as an endoscope, being set, are movable about a center near an insertion hole in which they are inserted as one unit and, since these instruments are moved about a center near the insertion hole, no undue force is imparted to the insertion hole of a subject without these instruments being displaced away from the center of the insertion hole and irrespective of the angle at which the instrument is inserted into the insertion hole.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a perspective view showing a holding apparatus according to a first embodiment of the present invention;

FIG. 2 is a perspective view showing a four-link parallelogram mechanism of the present apparatus;

FIG. 14 is a side view showing a holding apparatus according to a sixth embodiment of the present invention;

FIG. 15 is a side view showing a holding apparatus according to a seventh embodiment of the present invention;

DETAILED DESCRIPTION OF THE PREFERRED EMBODIMENTS

Figure 3A:
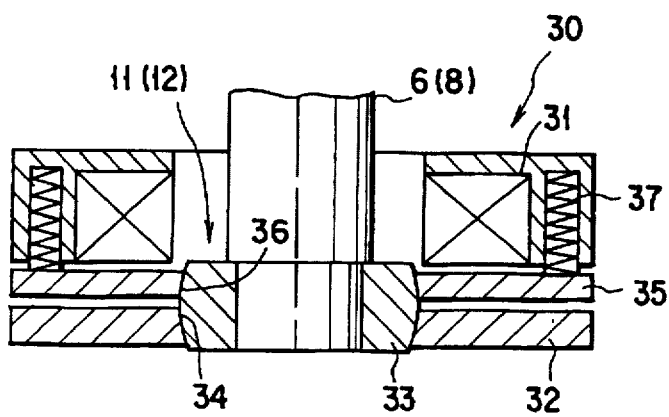
FIG. 3A shows a spherical bearing in an unlocked state.

A holding apparatus according to a first embodiment of the present invention will be explained below with reference to the accompanying drawings.

The present apparatus is used to hold, in place, a medical instrument, such as a laparoscope and treating instrument, which can perform an operation on a human abdominal cavity under the laparoscope. The present apparatus is comprised of a link mechanism.

Referring to FIGS. 1 and 2, a holder for holding the treating instrument, such as forceps, in place comprises a support arm 2 made up of a pipe. One end of each of upper and lower arm sections 4 and 5 are connected by pivots 3a and 3b to the upper and lower end portions of the support arm 2 such that these arm sections 4 and 5 are rotatable, while in a parallelogram form, in a plane including an axis of the support arm 2. An arm section 8 is mounted by pivots 7a and 7b at those areas near the other end of the upper and lower arm sections 4 and 5 such that these upper and lower arm sections 4, 5 are rotatable, while in a parallelogram form, in the plane as described above.

The support arm 2 holds a straight section of the treating instrument 1 in place so as to allow it to be moved up and down within the support arm (pipe) 2. For example, an elastic O ring, not shown, is provided in the inner surface of the pipe (support arm 2) so as to hold the straight section of the treating instrument 1 under an elastic force of the elastic O ring. When a force is applied to the treating instrument 1 in an axial direction, the straight section of the treating instrument can be moved back and forth relative to the support arm 2. The holding arrangement is not restricted only to the one as set out above.

The support arm 2, together with the upper and lower arm sections 4 and 5 and arm section 8, constitute a four-link parallelogram mechanism X. An auxiliary arm 6 parallel to the arm section 8 is mounted, by pivots 9 and 10, on the other ends of the upper and lower arm sections 4 and 5. That is, the upper and lower arm sections 4 and 5, arm section 8 and parallel arm 6 comprise to another four-link parallelogram mechanism connected to the four-link parallel mechanism The lower end sides of the arm section 8 and auxiliary arm section 6 extend in a direction parallel to the support arm 2. The extending end portions of the respective arm sections 6 and 8 are pivotally fitted around spherical bearings 11 and 12 mounted in a rotatable arm 14 of a support mechanism 13. That is, the four-link parallelogram mechanism X is supported on the rotatable arm 14 of the support mechanism 13 through the later-described four-link parallelogram mechanism. The spherical bearings 11 and 12 of the support mechanism 13 are so configured that they can rotate the parallelogram mechanism X in a parallelogram form about the line C, that is, rotate the parallelogram X about the line C. Thus the medical instrument can be rotated in all directions about a non-movable point. Thus the present apparatus is so configured that it allows the parallelogram-mechanism X which is provided integral with the arm section 8 and auxiliary arm section 6 to be rotated in all directions as will be seen from FIG. 1.

The support mechanism 13 comprises the rotatable arm 14 as set out above, a second arm 15 rotatable in an up/down direction and a stand 16. The stand 16 comprises a base 19 secured by a setscrew 17 to a bed 18 and a round support post 20 mounted upright on the base 19.

The other end side of the second rotatable arm 15 is mounted on the upper end of the support post 20 of the stand 16 such that the second arm 15 is rotatable about the support post 20. By tightening the setscrew 21 the rotatable arm 15 is fixed to the support post 20, restricting its rotational movement.

The rotatable arm 14 is so supported by a pivot 22 on the rotatable arm 15 as to be rotatable in an up/down direction. A setscrew 23 is provided on the rotatable arm 14 and, by tightening the setscrew 23 it is possible to restrict the rotation of the rotatable arm 14 relative to the rotation arm 15. At the upper surface of the rotatable arm 14 the spherical bearings 11 and 12 as set out above are provided, in a spaced-apart relation, in a longitudinal direction of the rotatable arm 14.

A downwardly extending portion 8a is provided, as an extension at the arm section 8 such that it extends through the spherical bearing 11. The extension 8a is a round bar-like member and has a weight 24, serving as a balance, at an area near its lower end. The weight 24 is movably fitted to extension 8a. The weight 24 is fixed by a setscrew 25 to a proper position.

An insertion hole (piercing hole) 28 (see FIG. 1) is formed in the abdominal wall 26 of a patient lying on a bed with a trocar 27 inserted in the hole. The treating instrument 1 is inserted into the trocar 27 and its distal end reaches into the abdominal cavity 29. Here P denotes a pivot point which is an intersecting point between a center line Z of the treating instrument 1 and the center of the insertion hole 28 and C, a straight line connecting the spherical bearings 11 and 12.

When the present apparatus is used, the positions in which the upper and lower arm sections 4 and 5 in the support mechanism 13 are rotated are so set that the intersecting point P and the straight line C meet each other. Since the supporting arm 2 and corresponding arm section 8 are equal in length and parallel to each other, an imaginary parallelogram Y (see FIG. 1) is created at all times together with the upper and lower arm sections and straight line C. With the parallelogram mechanism X displaced, the treating instrument 1 is rotated about the intersecting pivot point P (on a non-movable center axis) in the plane of the four-link imaginary parallelogram Y.

As shown in FIG. 3, the spherical bearings 11 and 12 have an electromagnetic type brake 30. The brake 30 has an electromagnetic coil 31 and bearing support plate 32 fixedly mounted on the rotatable arm section 14. The bearing support plate 32 has a spherical bearing face 34 for receiving a spherical bearing 33 provided relative to the lower ends of the arm sections 6 and 8. A clutch plate 35 made of a magnetic material is provided between the electromagnetic coil 31 and the bearing support plate 32 such that the clutch plate 35 can be moved in an up/down direction. The clutch plate 35 has a spherical bearing face 36, as a hole, conforming to the surface of the spherical bearing 33. The brake 30 has a locking function for suppressing the displacement of the parallel link mechanism and constitutes a mechanism for rotating the medical instrument and parallel link mechanism, as one unit, along a line passing through the non-movable point.

The clutch plate 35 is downwardly urged by a spring 37 and, since the coil 31 being normally demagnetized, it is downwardly depressed as shown in FIG. 3A, pushing the spherical bearing face 36 of the clutch plate 35 toward the surface of the spherical bearing 33 and hence suppressing the rotation of the arm sections 6 and 8.

Figure 3B:
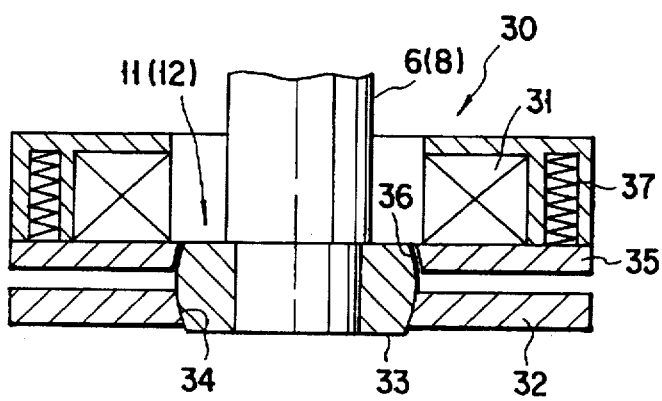
FIG. 3B shows the spherical bearing in the locked state.
Figure 4:
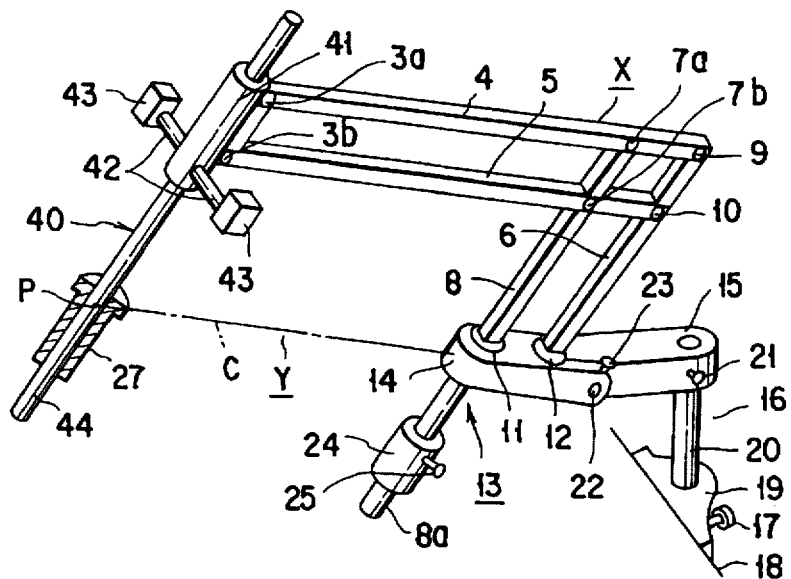
FIG. 4 is a perspective view showing a holding apparatus according to a second embodiment of the present invention.

With the electromagnetic coil 31 magnetized, the clutch plate 35 downwardly urged by the spring 37 is raised as shown in FIG. 3B, unlocking the clutch plate 35 and bearing surface 36 so that the arm sections 6 and 8 can be freely rotated, in all directions, about the spherical bearings 11 and 12.

The releasing and locking of the brake is the readily switched by rendering the electromagnetic type brake 30 ON and OFF.

In the electromagnetic clutch type brake 30, the clutch plate 35 is brought into locking engagement with the bearing 33 through direct contact with each other. Alternatively, the bearing 33 may be clamped by a clutch, etc., instead of directly bringing the clutch plate 35 into direct contact with the bearing 33.

The weight 24 is of such a type that, when the electromagnetic clutch type brake 30 is released, balance can be achieved so that the four-link parallelogram is not broken, or the four-link parallelogram mechanism falls down, by the weight of the treating instrument 1. With the four-link parallelogram mechanism X displaced, gravitational balance can be achieved anywhere at its parallel four-link structure. A relation of a balancing mechanism will now be explained below with reference to FIG. 2.

In FIG. 2, $m_1$ represents a center of gravity of the upper and lower arm sections 4 and 5; $m_2$, a center of gravity of the arm sections 6 and 8; $m_3$, the position of a center of gravity of the treating instrument 1; and M, a center of gravity of the weight 24. These are also represented by their weights $m_1$, $m_2$, $m_3$ and M. Let $L_1$, $L_2$, $L_3$ and L represent the lengths of perpendiculars from these centers of gravity, $m_1$, $m_2$, $m_3$ and M to the straight line C, respectively. Then in order to satisfy an equation (1) given below $$L_1 \cdot m_1 + L_2 \cdot m_2 + L_3 \cdot m_3 = L \cdot M \tag{1}$$

the weight M of the weight 24 is varied or the length L is varied by loosening the setscrew 25 of the weight 24 and adjusting the fixed position of the weight 24. By so doing, adjustment is made to obtain gravitational balance in the four-link parallelogram mechanism X.

The operation of the present apparatus will be explained below.

The setscrews 17, 21 and 23 are loosened and the base 19 of the support mechanism 13 is properly moved and the arm 14 and 15 are rotated. By so doing, the treating instrument 1 supported by the support arm 2 in the four-link parallelogram mechanism X is inserted into the trocar 27 inserted into the insertion hole 28 of the abdominal cavity. The supporting mechanism 13 is rotatably operated such that the intersecting point P between the center line Z of the treating instrument 1 and the center of the insertion hole 28 meets the straight line C connecting together the spherical bearings 11 and 12. Then, the four-link parallelogram mechanism is set and fixed by tightening the setscrews 17, 21 and 22.

In the set position, the parallelogram is maintained at all times even when the treating instrument 1 is tilted relative to the horizontal or even when an operation is performed in a two-dimensional direction in the parallelogram plane Y. This can be achieved irrespective of the angle at which the treating instrument 1 is inserted. In this case the point P is at all times not displaced away from the center of the insertion hole 28. That is, the point P is set in a locked state (i.e., it is a non-movable point). Therefore no undue force acts upon the insertion hole 28 even if the treating instrument 1 is moved by utilizing the four-link parallelogram mechanism X.

Further since the four-link parallelogram mechanism X is balanced with the weight 24 on the extension 8a of the arm section 8, that balance is not broken when the electromagnetic clutch type brake 30 is released; that is, even when the arm sections 6 and 8 are released from their locked state. It is thus possible to set and maintain the four-link parallelogram stable. There is also no possibility that the treating instrument 1 will be dropped down from the held position under its own weight.

FIGS. 4 to 10 show an apparatus according to a second embodiment of the present invention.

The second embodiment is substantially the same as the first embodiment except that, in the second embodiment, a scope-holding section 41 for holding a rigidoscope 40 is provided instead of the support arm 2 for holding the treating instrument 1, and a pair of index mark projecting devices 43 are mounted one to the left and one to the right of an arm 42 of the scope-holding section 41.

Figure 9:
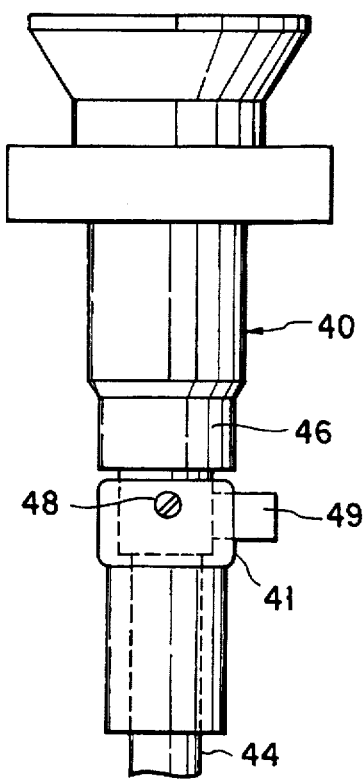
FIG. 9 is a front view showing a scope-holding section in the second embodiment.
Figure 10:
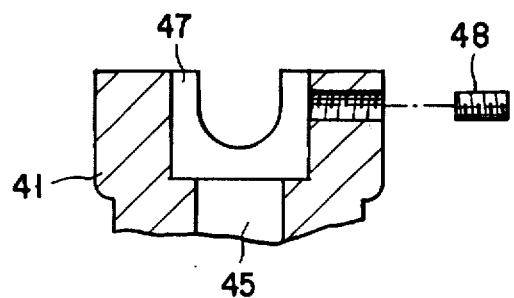
FIG. 10 is a cross-sectional view showing the scope-holding section in the second embodiment.

As shown in FIGS. 9 and 10, the scope-holding section 41 has a first hole 45 for inserting a straight tube section 44 of the rigidoscope 40 and a second hole 47 of a relatively large diameter for inserting a forward end of a proximal end section 46 of the rigidoscope 40, the two holes 45 and 47 being formed in a coaxial relation. A setscrew 48 is provided for fixedly securing the proximal end section 46 of the rigidoscope 40 at the scope-holding section 41 with the rigidoscope 40 inserted into the scope-holding section 41. A connector 49 is projected from the side surface of the proximal end section 46 of the rigidoscope 40 so as to allow connection of a light guide cable, not shown.

Figure 6:
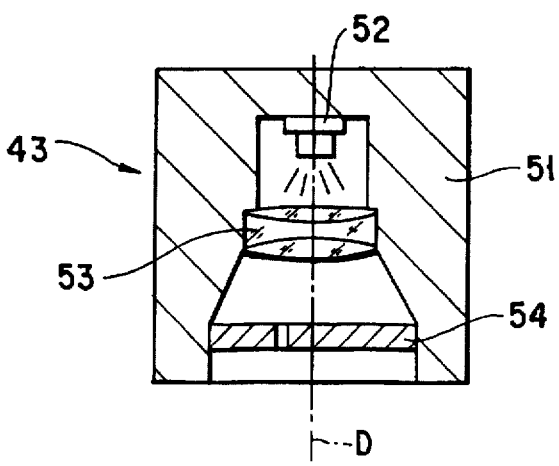
FIG. 6 is a cross-sectional view showing an index-mark projecting device in the second embodiment.
Figure 7:
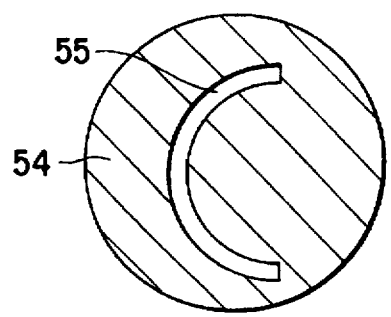
FIG. 7 is a plan view showing a light shielding plate of the index mark projecting device in the second embodiment.

The projecting devices 43 are so constructed as shown in FIG. 6. Stated in more detail, a housing 51 is connected to each free end of the connection arm 42 and equipped with a semiconductor laser 52 for emitting red light of a visible range, a beam expander 53 and a light shielding plate 54. The light shielding plate 54 has a semi-annular light transmitting area 55 as shown in FIG. 7. The shapes of the light transmitting areas 55 of the respective projecting devices 43 are opposite in their direction. In the respective projecting device 43, a light beam exiting from the semiconductor laser 52 is enlarged by the beam expander 53, transmitted through the light shielding plate 54 and projected, as a parallel beam, that is, as an index mark 57 conforming to the shape of the light shielding area 55.

Figure 5:
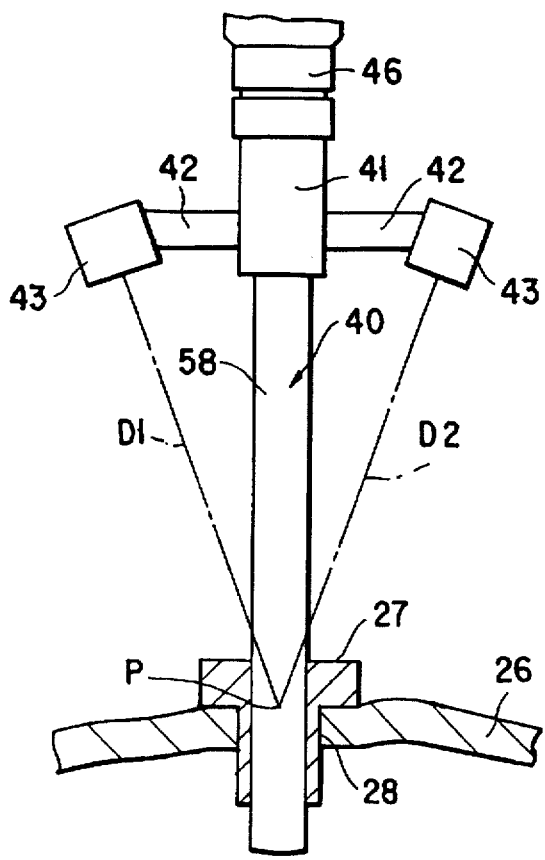
FIG. 5 is a front view as viewed from near a scope-holding section of the second embodiment.

FIG. 5 shows a positional relation between the rigidoscope 40 inserted through the trocar 27 and the projecting devices 43, right and left. The right and left projecting devices 43 have their projecting optical axes $D_1$ and $D_2$ positioned in a right/left symmetrical relation to an observation optical axis 58 of the rigidoscope 40 and are mounted at those angles at which the intersecting point of the projecting optical axes $D_1$ and $D_2$ is so set as to meet at the center point P as set out above.

Figure 8A:
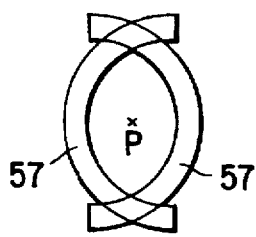
FIG. 8A is an explanatory view showing the index mark projected.
Figure 8B:
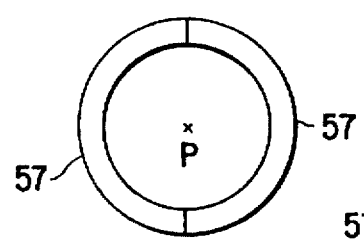
FIG. 8B is an explanatory view showing another index-mark projected.

The projecting devices 43, being so mounted at a predetermined angle as to secure such a symmetry to the observation optical axis 58, allow their index marks 57 which are projected through their light shielding plates 54 to define a configuration as shown in FIG. 8B, provided that the index marks are projected on a substantially horizontal plane including the point P. That is, these index marks 57 are projected past the light transmitting areas 55 of the light shielding plates 54 such that both the ends of the index marks meet each other to provide a true circle, as a projection image, with the point P as a center. If the condition as set out above is not satisfied, the projection image becomes one as shown in FIG. 8A or 8C.

After the trocar 27 has been thrust into the abdominal cavity 26, the straight section 44 of the rigidoscope 40 is inserted into the trocar 27 with the rigidoscope 40 mounted on the scope-holding section 41. Then, with a switch, not shown, ON, the laser beams emitted from the semiconductor lasers 52 of the projecting devices 43 are enlarged by the beam expanders 53 and projected past the light transmitting areas 55 of the light shielding plates 54 toward the point P, that is, projected as the index marks conforming to the shape of the light transmitting area 55.

Figure 8C:
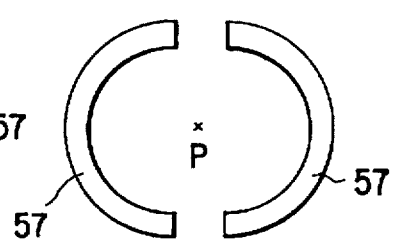
FIG. 8C is an explanatory view showing another index mark projected.

In this case, a projection image of an object at the point P, that is, at a site in the projection plane becomes either of ones as shown in FIG. 8A, 8B and 8C. FIG. 8A shows the case where an object is located at a site nearer than the point P; FIG. 8B, an object at a site meeting the center point P; and FIG. 8C, an object at a site farther than the center point P. An operator moves the arm assembly of the support mechanism 13 to a position as shown in FIG. 8B where the right and left index marks 57 projected from the projecting devices 43 take on a circular configuration with its center meeting the center point P of that insertion hole 28 of the abdominal wall 26 where the trocar 27 is thrust (inserted). After the arm assembly has been so positioned, the associated arms 14 and 15 are locked in place by tightening the respective setscrews 17, 21 and 23.

From the relation of the two index marks relative to each other, it will be readily known in which direction the center point P of the rigidoscope 40 is displaced. It is thus possible to make prompt adjustment. Since the insertion point of the trocar 27 has only to meet the center position of a circle defined by the resultant index marks 57, the index mark 57 is not subject to "vignetting".

Figure 11:
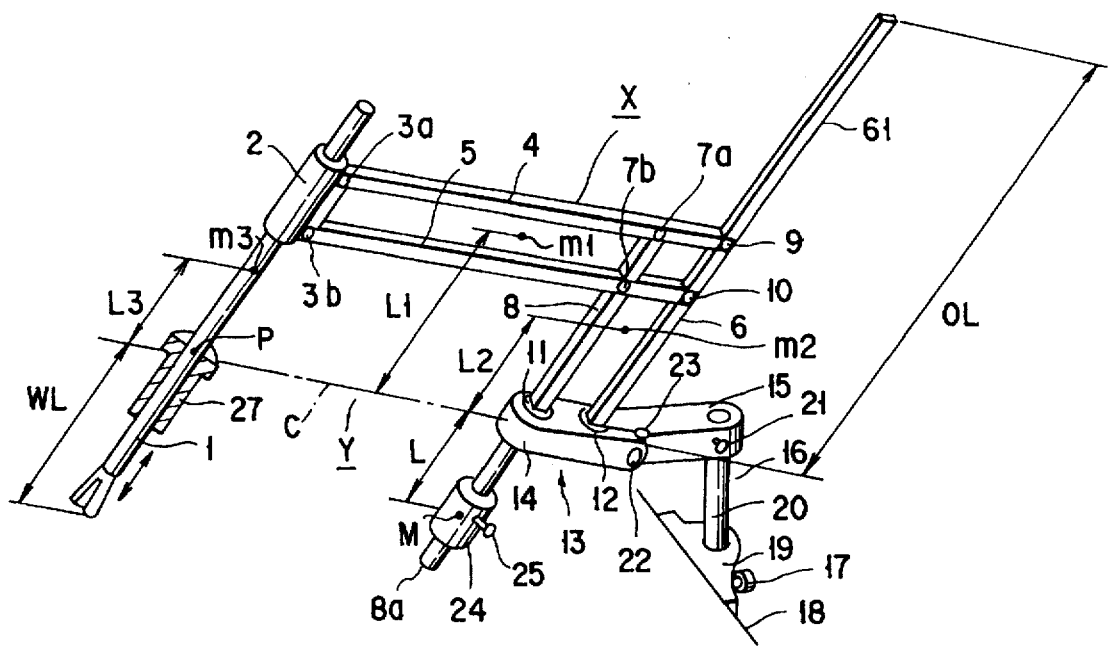
FIG. 11 is a perspective view showing a holding apparatus according to a third embodiment of the present invention.

FIG. 11 shows a holding apparatus according to a third embodiment of the present invention, which is, a variant of the first embodiment. In this embodiment, an operation handle 61 is provided on a corresponding arm of a four-link parallelogram mechanism X. An auxiliary arm 6 is upwardly extended to provide an extension constituting the aforementioned operation handle 61. The operation handle 61 defines a length OL from a straight line C to pass on the point P set out above. The length OL is set to be longer than a length WL from the center point P to the distal end of the treating instrument 1 or a medical instrument such as an endoscope.

With the operation handle 61 thus provided, it is possible to readily adjust the position of the treating instrument 1 or the medical instrument and hence to readily make accurate, fine adjustment by a simpler operation because the length OL is set to be longer than the length WL.

Figure 12:
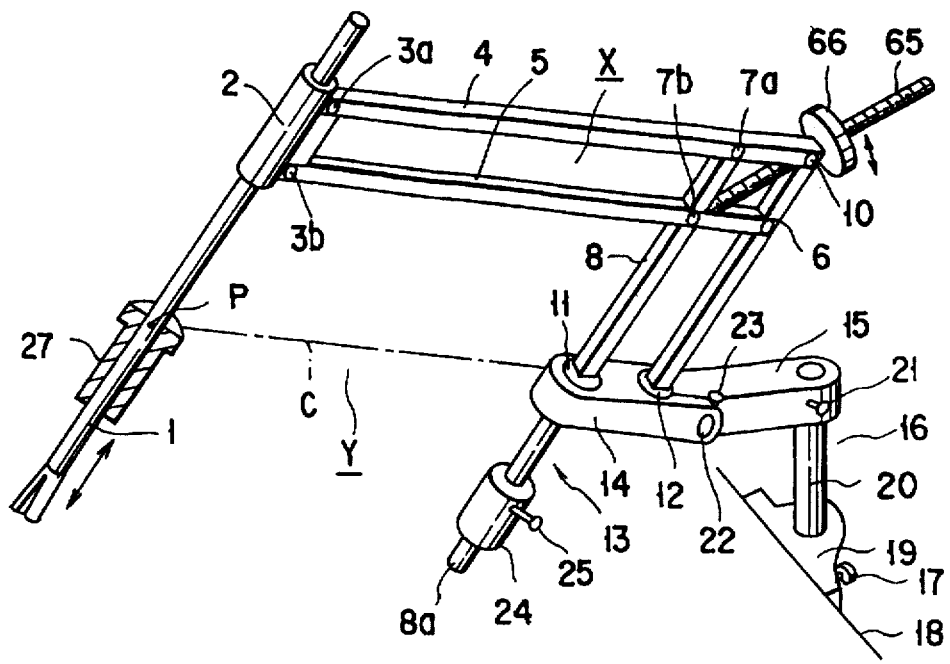
FIG. 12 is a perspective view showing a holding apparatus according to a fourth embodiment of the present invention.

FIG. 12 shows a fourth embodiment of the present invention, which also is a variant of the first embodiment. In this embodiment, a means is provided for adjusting the length of a diagonal line of a given parallelogram of a four-link parallelogram mechanism X. Stated in more detail, a bar-like screw member 65 is provided, as the adjusting means, at given diagonal opposed corners of a given parallelogram created by upper and lower arm sections 4 and 5 as well as an auxiliary arm section 6 and arm section 8. One end of the screw member 65 is pivoted to the corner area defined by the lower arm section 5 and arm section 8 and the other end portion of the screw member 65 extends through the corner area defined by the upper arm section 4 and auxiliary arm section 6 and an adjusting nut 66 is threaded over the other end side of the screw member 65 at an outer area corresponding to an outer corner of the given parallelogram.

The length of the diagonal line of the parallelogram created by the arm sections 4,5 and 6,8 can be varied by varying the position to which the adjusting nut 66 is threadably fixed. By adjusting the length of the diagonal line the corresponding parallelogram of the four-link mechanism X is varied to an adjusted position. That is, the length of that diagonal line of the parallelogram can be varied by the position to which the nut 66 is fixed, so that it is possible to readily and finely adjust the position of the treating instrument and medical instrument such as the endoscope.

Figure 13:
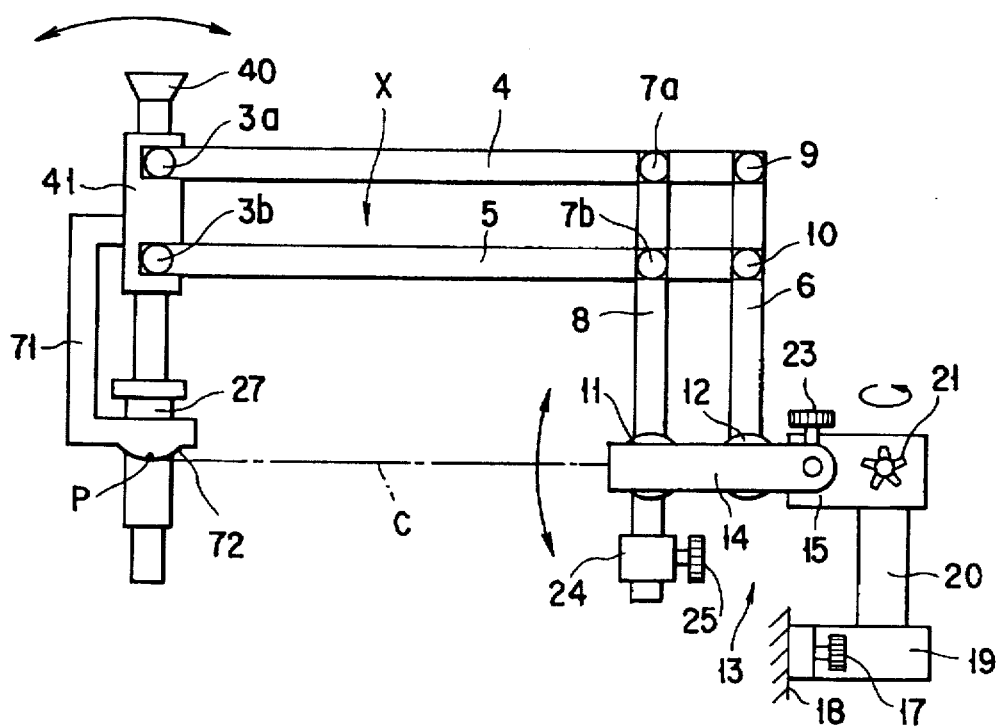
FIG. 13 is a side view showing a holding apparatus according to a fifth embodiment of the present invention.

FIG. 13 shows a fifth embodiment of the present invention. The fifth embodiment is substantially similar to the first embodiment except in the following points. That is, a scope-holding member 41 for holding a rigidoscope 40 is provided in place of the support arm 2 for holding the treating instrument 1. An L-shaped trocar-holding arm 71 is mounted on the scope-holding member 41 so as to hold the trocar 27 in place. The trocar holding arm 71 has a bulbous portion 72 whereby it is possible to locate a center point p. The trocar 27 is held coaxial with the rigidoscope 40. Here the point of support of one of the links in a defined parallelogram is provided as a substantial center point P.

According to the fifth embodiment of the present invention, when scope-holding member 41 is tilted, then the trocar holding arm 71 is tilted about the center point P, while following the motion of the holding member 41. That is, either the trocar 27 or the rigidoscope 40 is tilted in an interlocking way.

After the trocar 27 has been thrust (inserted) into the abdominal wall 26, the trocar holding arm 71 is lowered together with the scope-holding member and the trocar 27 is held in place with the bulbous portion 72 applied to the surface of the abdominal wall of the patient. Then the rigidoscope 40 is inserted over a length from the scope-holding member 41 to the trocar 27. For the other functions the fifth embodiment is similar to the first embodiment.

According to the construction as set out above, the apparatus can readily be set in place because the center point P of the rigidoscope 40 corresponds to a point where the bulbous portion 72 of the trocar-holding arm 71 is set in contact with the surface of the abdominal wall of the patient. The trocar 27 is held with the trocar-holding arm 71 coupled to the scope-holding member 41 and, even if use is made of a heavier trocar in general, is not naturally displaced into the abdominal cavity. Further since the trocar-holding arm near the upper surface of the body of the patient is made neat and smooth, there is no obstacle upon surgery.

FIG. 14 shows a sixth embodiment of the present invention. In this embodiment, the lower arm section 5 of the four-link parallelogram mechanism X in the fifth embodiment is replaced with a lower arm section 75 provided between the lower end of a bulbous portion 72 of the trocar-holding arm 71 and the rotatable arm 14 of the support mechanism 13 of the fifth embodiment. The scope-holding member 41 is formed integral with a trocar-holding arm 71.

A clamp knob 76 is mounted on the scope-holding member 41 to fix the rigidoscope 40 in engagement with the scope-holding member. A clamp knob 77 is also mounted on the lower end side of the tracer holding arm 71 to fix the trocar 27. The lower arm section 75 of the four-link parallel mechanism X is retracted toward an upper arm section 4 side to provide an intermediate section parallel to the upper arm section. Therefore, this imparts no obstacle to the operator during operation. Further no auxiliary arm 6 is provided to the four-link parallel mechanism X.

A bearing 78 is interposed partway of the rotatable arm 14 of the support mechanism 13 for supporting the four-link parallel mechanism X, whereby it is possible to rotate the four-link parallel mechanism X about a straight line C so that this motion can be imparted to the medical instrument. The four-link parallel mechanism X can be tilted about the center point P in a four-link parallel plane and be tilted while rotating along the straight line C. That is, the medical instrument is tiltable about the center point P in the two combination directions. The whole motion balance of the four-link parallel mechanism X can be achieved by a weight 24.

According to this instruction, a rotational motion of the medical instrument about one point can be achieved by the four-link parallel mechanism X (four arm sections) and bearing 78. It is thus possible to provide an apparatus which is simpler in construction as a whole.

Alternatively, another support mechanism may be constructed by supporting the mechanism X-supporting structure by an additional up/down displaceable four-link parallel mechanism and fixing the additional mechanism to a bed, etc., by a shaft which is rotatable about a vertical axis.

FIG. 15 shows a seventh embodiment of the present invention. In this embodiment, a trocar-supporting arm 81 is provided on the rotatable arm 14 of the support mechanism 13 in the first embodiment. The trocar-holding arm 81 supports, at its forward end, a ball 83 which has a through-hole 82 passing through a center point 82. The ball 83 is so held as to be rotatable in all directions relative to the trocar-holding arm 81. The straight section of the trocar 27 is inserted through the through-hole 82 of the ball 83 and held there.

The trocar-holding arm 81 comprises a first arm section 84 on the rotation arm 14 side and second arm section 85 for supporting the ball 83. The first and second arm sections 84 and 85 are rotatable about a shaft 86, as indicated by an arrow in FIG. 15, in a direction intersecting the parallel plane of a four-link parallelogram mechanism X and are fixed by a setscrew 87 against their relative rotation. The apparatus is positioned with the portion of the ball 83 applied to the abdominal wall of the patient.

After the trocar 27 has been inserted through the through hole 82 of the ball 83, it is thrust (inserted) into the abdominal wall and the setscrew 87 is tightened so as to set the first and second arm sections 84 and 85 in a straight line relation, that is, to locate the center of the ball 83 on a center point P. By so doing, these arm sections 84 and 85 are fixed by the setscrew 87 so as to prevent any movement of the trocar-holding arm 81. Then, a rigidoscope 40 is inserted from a scope-holding section 41 into the trocar 27. By so doing, the rigidoscope 40 and trocar 27 are rotatable with about the center point P and are tiltable.

According to the construction described above, since the trocar-holding arm 81 is comprised of the first and second arm sections 84 and 85, it is possible to not only obtain the advantages of the first embodiment but also rotate these arm sections about the shaft 86. The trocar 27, rigidoscope 40, etc., can be moved, as required, away from any position where there is an obstacle during operation.

Figure 16:
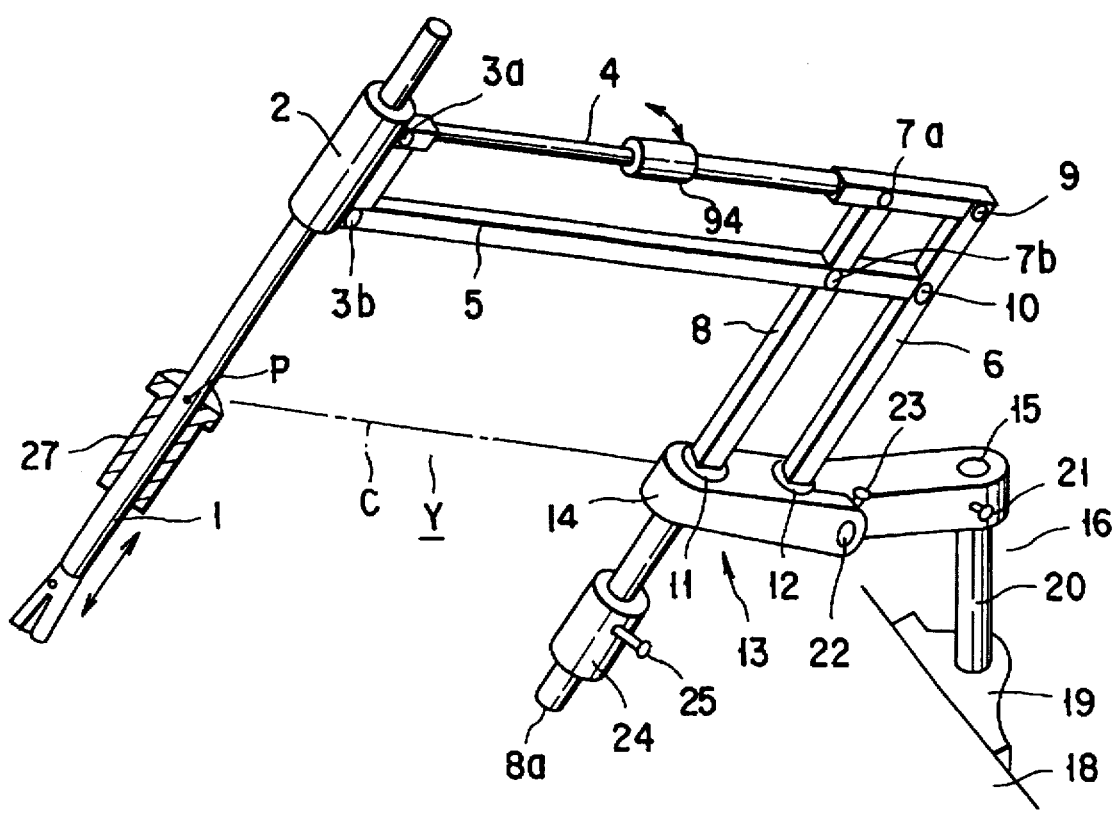
FIG. 16 is a perspective view showing a holding apparatus according to an eighth embodiment of the present invention.
Figure 17:
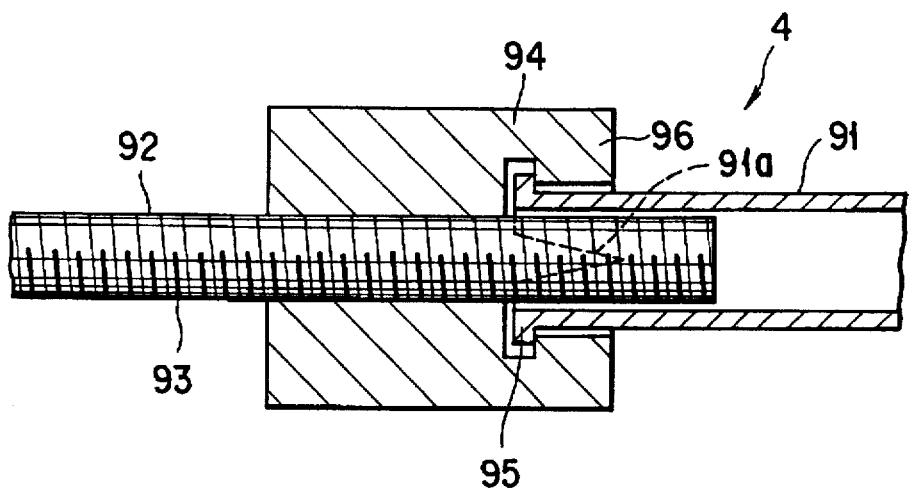
FIG. 17 is a cross-sectional view showing an adjusting means for adjusting the length of an upper arm section in the embodiment.

FIGS. 16 and 17 show an eighth embodiment of the present invention. In this embodiment, a mechanism is provided for adjustably varying the length of at least one of the arms of the four-link parallelogram mechanism X so that a proper arm length can be selected. It is, here, possible to adjust the length of the upper arm section 4. For the other parts the eighth embodiment is similar to the first embodiment.

As shown in FIG. 17, the upper arm section 4 comprises an outer pipe 91 and inner bar 92. The inner bar 92 is inserted into the outer pipe 91 and so connected as to adjust the extent of insertion. An externally threaded section 93 is provided on the outer periphery of the inner bar 92 and a nut 94 is threaded over the externally threaded portion of the threaded section 93. An inwardly extending flange 96 is provided on the nut 94 and latched to a latching section 95 comprised of a flange formed on the forward end edge of the external pipe 91. The forward end portion of the outer pipe has a cutout 91a as indicated by the dot line in FIG. 17 so that it can be elastically diameter-reduced and, when the latching section 95 is inserted into the nut 94, the forward end portion of the outer pipe is diameter-reduced to allow the nut 94 to be inserted into the flange 96.

When the nut 94 is rotated over the externally threaded section 93 of the inner bar 92, the inner bar 92 together with the outer pipe 91 is moved in the axial direction of the inner bar 92 and, by so doing, the extent of insertion of the inner bar 92 into the outer pipe 91 can be adjusted so that the effective length of the upper arm section 4 can be properly adjusted. It is thus possible to adjust the length of the arm of the four-link parallelogram mechanism X.

Figure 18:
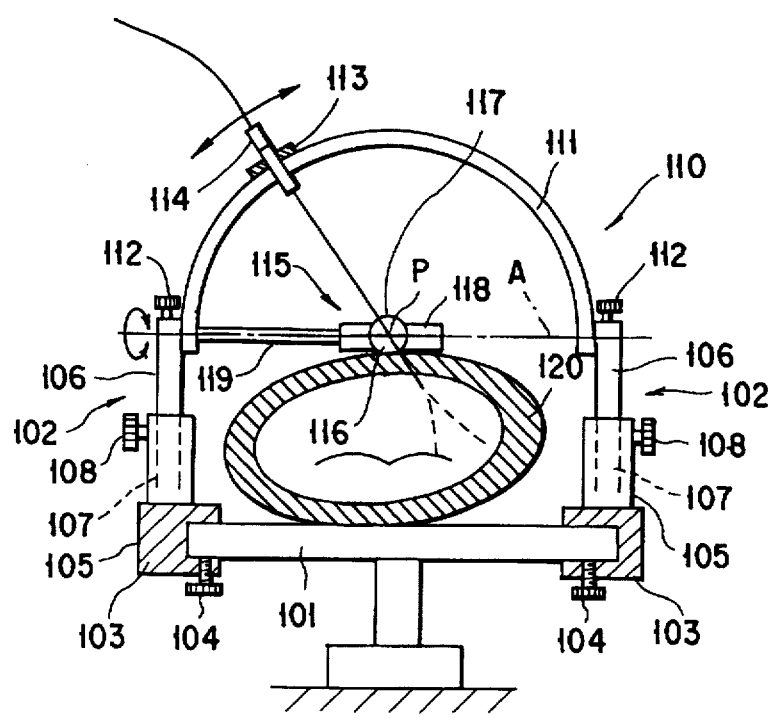
FIG. 18 is an explanatory view showing a holding apparatus according to a ninth embodiment of the present invention.

FIG. 18 shows an apparatus according to a ninth embodiment of the present invention. In FIG. 18, reference numeral 101 shows a bed on which the patient lies. Support level adjusting mechanisms 102 are provided one at the right side edge and one at the left side edge of the bed 101. The support level adjusting mechanism 102 has a clamping tool 103 for sandwiching the side edge portion of the bed 101 so that it is secured to the side edge portion. At the selected fastening positions of the clamping tools a corresponding setscrew 104 is fastened to the bed 101 so that the clamping tool is fixed at these selected positions.

A first adjusting shaft 105 is uprightly provided on the clamping tool 103 and a second adjusting shaft 106 is slidably inserted in a coaxial direction of the first adjusting shaft 105 and connected to the first adjusting shaft. That is, the first adjusting shaft 105 has a coaxial bore 107 into which the lower end portion of the second adjusting shaft 106 is inserted. The height of the second adjusting shaft 106 can be controlled by adjusting the extent to which the second adjusting shaft 106 is inserted into the bore 107 of the first adjusting screw 105. At that time, a setscrew is tightened to achieve the proper extent of insertion and hence the height of the second adjusting shaft. A setscrew 108 is provided in the first adjusting shaft 105 to fix the second adjusting shaft 106 in place in the bore 107.

A mechanism 110 for holding the medical instrument is mounted on the support level adjusting mechanism 102. The instrument-holding mechanism 110 has a guide arm 111 extending between the forward end portions of those second adjusting shafts 106. The respective end portions of the guide arm 111 are pivotally supported at the forward end portions of the second adjusting shafts 106 so that the guide arm 111 can be turned along a center line A joining these pivotal points. The center line A is normally near-horizontal. The guide arm 111 can be restricted against a turn when the pivots at both the end portions of the guide arm 111 are tightened by setscrews 112.

The guide arm 111 is formed as a semicircular arm having a diameter corresponding to a end-to-end distance of the center line including the center of a turn. A slide member 113 is so provided on the guide arm 111 as to allow it to be slidably moved along the guide arm 111. The slide member 113 holds, for example, a rigidoscope as a medical instrument 114.

A restricting tool 115 is located in the semicircular center position of the guide arm 111 and has a ball-like rotation member 117 with a through bore 116 through which the straight section of the rigidoscope 114 extends. The rotation member 117 supports the rigidoscope 114. The rotation member 117 is journalled in a bearing member 118 so that it can be rotated. The bearing member 118 is coupled by a shaft member 119 to the guide arm 111.

In use, the height from the bed 101 to a thrusting (inserting) position of a patient's abdominal wall 120 is adjusted by the first and second adjusting shafts 105 and 106 in the support level adjusting mechanism 102. The restricting tool 115 is set in the thrusting position on the abdominal wall 120 of the patient by adjusting the horizontal position by the clamping tool 103. The rigidoscope 114 is mounted in the slide member 113 and the straight section of the rigidoscope 114 is inserted through the insertion bore 116 of the rotation member 117 in the restricting tool 115. It is to be noted that, when a trocar is used, the straight section of the rigidoscope 114 is inserted through the trocar.

Even when the slide member 113 is moved along the guide arm 111, the center point P of the rotation member 117 is not displaced. Even if the guide arm 111 is tilted, the rotation center line A passes through the center line P and hence the center point P is not displaced. The direction in which observation is made can be varied by tilting the straight section of the rigidoscope 114 in a varying direction with the center point P as a center. Since, in this case, the center point P is not displaced upon tilting the rigidoscope, no undue force is exerted on the insertion hole of the abdominal wall 120.

Figure 19:
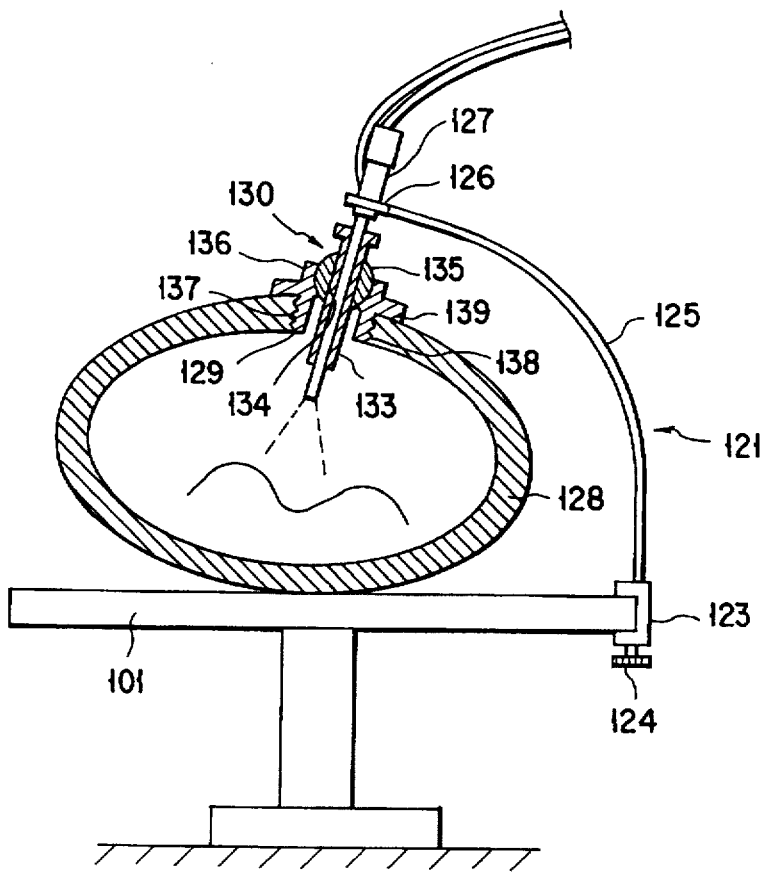
FIG. 19 is an explanatory view showing a holding apparatus according to a tenth embodiment of the present invention.

FIG. 19 shows an apparatus according to a tenth embodiment of the present invention. In FIG. 19, reference numeral 101 represents a bed on which the patient lies. A support mechanism 121 is mounted on one side of the bed 101 and has a champing tool 123 adapted to clamp the side edge portion of the bed 101. The clamping tool 123 has a setscrew 124 for fixing it to the bed 101. The clamping tool 123 is fixed to a selected position on the bed by tightening the setscrew 124 relative to the bed via the clamping tool.

A semi-rigid support arm 125 is mounted upright on the clamping tool 123. Here the word "semi-rigid" is used to mean that the semi-rigid arm 125 is bent by applying an external force of a certain extent to the arm 125 by hand, etc., but maintains its set state, without being deformed, when the medical instrument or the like is normally supported. A holding tool 126 is mounted on the forward end of the support arm 125 to hold the medical instrument in place. The holding tool 126 holds, for example, a rigidoscope 27 in place.

A restricting tool 130 is mounted relative to a thrusting (inserting) position on the abdominal wall 128 of the patient. A ball-like rotation member 135 is provided in the restricting tool 130 and has a through bore 134 through which a trocar 133 is inserted with the straight section of the rigidoscope 127 inserted therein. The rotation member 135 is journaled in a bearing member 136 such that it can be rotated in all directions. The bearing member 136 is comprised of a cylindrical member 137 to be thrust (inserted) into the through hole 129 in the abdominal wall 128 of the patient, noting that an externally threaded section 138 is provided on the outer periphery of the cylindrical member 137. A flange 139 is formed on the outer end portion of the cylindrical member 137 to be set in contact with the outer surface of an abdominal wall 128 of the patient.

A mechanism is provided between the bearing member 136 and the ball-like rotation member 135 so that it restricts some movement while hermetically sealing at an area between these members 136 and 135. As the mechanism, use may be made of a frictional member, or a balloon to be expanded under gas pressure created with a supply of air, water, etc., or an electrically driven means such as an electromagnetic clutch.

In use, the cylindrical member 137 is inserted into the insertion hole 129 at the abdominal wall 128 of the patient. The rigidoscope 127 is held in the holding tool 126 of the support arm 125 and the straight section of the rigidoscope 127 is inserted into the trocar 133 which is inserted into the through hole 134 of the bearing member 136. Since the support arm 125 is semi-rigid, the tilt at which the tool (126)-holding rigidoscope 127 together with the trocar 133 is held can freely be varied.

At this time, the ball-like rotation member 135 is rotated at its center corresponding to the center point P. With the center point P as the reference, the straight section of the rigidoscope 114 can be tilted in varying directions and it is possible to vary the direction in which observation can be made. Since the tilt center point P is set at an area near the insertion hole 134 in the abdominal wall 128, no undue force is exerted on the abdominal wall 128 of the patient.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An apparatus for holding a medical instrument in place when a medical operation is to be performed on a subject at an operation field in the subject, with the medical instrument inserted into an insertion hole of a body wall of the subject, which insertion hole provides access to said operation field, the apparatus comprising:

holding means for holding the medical instrument in place;

a fixing device defining a fixing position which is located separate and apart from the subject; and locating means coupled between the holding means and said fixing device defining said fixing position, for locating the holding means at a position near the subject and significantly separate from the operation field;

said locating means including a rotating mechanism which rotatably supports the holding means adjacent the operation field such that the medical instrument which is held by the holding means is rotatable about a fixed, non-movable, pivot point which is located near the insertion hole of the body wall, with the medical instrument, through the holding means, being rotatable about the fixed, non-movable, pivot point, without applying reaction forces to the body of the subject.

2. The apparatus according to claim 1, wherein the rotating mechanism comprises a parallel link mechanism.

3. The apparatus according to claim 2, further comprising a locking mechanism coupled to said parallel link mechanism for restricting displacement of the parallel link mechanism with the holding means held in a locked state, and for setting the parallel link mechanism in a locked state.

4. The apparatus according to claim 2, wherein the parallel link mechanism comprises link arms for holding the medical instrument at a non-movable point, said link arms corresponding to links of the parallel link mechanism.

5. The apparatus according to claim 2, further comprising:

operation means coupled to said parallel link mechanism for adjusting a diagonal length defined by arms in the parallel link mechanism to displace the parallel link mechanism so that the medical instrument is rotated to a set position.

6. The apparatus according to claim 2, wherein said parallel link mechanism comprises four links interconnected to form a parallelogram in a single plane.

7. The apparatus according to claim 1, further comprising a balance mechanism coupled to said rotating mechanism for stably maintaining the rotating mechanism at any stopped position so that the medical instrument is held at the stopped position.

8. The apparatus according to claim 7, wherein said parallel link mechanism comprises four links interconnected to form a parallelogram in a single plane.

9. The apparatus according to claim 8, wherein said balance mechanism comprises an extension of one of said four links of said parallel link mechanism, and a weight member mounted on said extension such that a position of said weight member on said extension is variable along a length of said extension.

10. The apparatus according to claim 1, wherein the rotating mechanism comprises:

a rotation member which supports said holding means so as to locate the medical instrument at a position near the insertion hole; and a bearing member for supporting the rotation member such that the rotation member is rotatable about the fixed non-movable pivot point.

11. The apparatus according to claim 1, further comprising an illumination device coupled to the holding means, said illuminating device projecting a plurality of index marks at corresponding different positions, and which indicates the fixed, non-movable, pivot point with the index marks projected on the body wall of the subject, thereby indicating a set position.

12. The apparatus according to claim 1, further comprising a handle coupled to the rotating mechanism for performing a displacing operation on the rotating mechanism, for thereby rotating the medical instrument.

13. The apparatus according to claim 1, wherein:

the rotating mechanism includes an arcuate guide arm with said fixed, non-movable, pivot point as a center; and said holding means is movable along the arcuate guide arm, whereby the medical instrument is rotated.

14. The apparatus according to claim 1, wherein said rotating means comprises first and second parallel link mechanisms coupled to each other, each of said parallel link mechanisms comprising four links arranged in the form of a parallelogram, at least one of said links being common to said first and second parallel link mechanisms.

15. An apparatus for holding a medical instrument in place when a medical operation is to be performed on a subject at an operation field in the subject, with the medical instrument inserted into an insertion hole of a body wall of a subject, which insertion hole provides access to said operation field, the apparatus comprising:

holding means for holding the medical instrument in place;

a fixing device defining a fixing position which is located separate and apart from the subject; and locating means coupled between the holding means and said fixing device defining said fixing position, for locating the holding means at a position near the subject and significantly separate from the operation field;

said locating means including:

a parallel link mechanism supporting the holding means such that the medical instrument which is held by the holding means is rotatable about a fixed, non-movable pivot point which is located near the insertion hole, the medical instrument being rotatable through the holding means about the fixed, non-movable, pivot point in a plane passing through the fixed, non-movable, pivot point which substantially corresponds to a rotation center of the medical instrument;

a rotating mechanism supporting the parallel link mechanism for rotating a plane of the parallel link mechanism about a line passing through the fixed, non-movable, pivot point; and means for setting the parallel link mechanism and the rotating mechanism so that the fixed, non-movable, pivot point is set at a predetermined position near the insertion hole.

16. The apparatus according to claim 15, wherein the rotating mechanism comprises at least one spherical bearing supported by the setting means and rotatably supporting the parallel link mechanism.

17. The apparatus according to claim 15, further comprising:

a first locking mechanism coupled to said parallel link mechanism for restricting displacement of the parallel link mechanism with the holding means held at a stopped position, and for setting the rotating mechanism in a locked state; and a second locking mechanism for suppressing displacement of the setting means at any free position, and for setting the setting means to a given locked position.

18. The apparatus according to claim 15, wherein said parallel link mechanism comprises four links interconnected to form a parallelogram in a single plane.

* * * * *